US00PP28473P3

(12) United States Plant Patent

Preil et al.

(10) Patent No.: US PP28,473 P3
(45) Date of Patent: Oct. 3, 2017

(54) ***RHODODENDRON* PLANT NAMED 'MICROHIRS3'**

(50) Latin Name: ***Rhohodendron* hybrid**
Varietal Denomination: Microhirs3

(71) Applicant: INKARHO GmbH, Bad Zwischenahn (DE)

(72) Inventors: Walter Preil, Ahrensburg (DE); Ralf Lüttmann, Bad Zwischenahn (DE)

(73) Assignee: Inkarho GmbH, Bad Zwischenahn (DE)

( * ) Notice: Subject to any disclaimer, the term of this patent is extended or adjusted under 35 U.S.C. 154(b) by 34 days.

(21) Appl. No.: 14/756,176

(22) Filed: Aug. 12, 2015

(65) Prior Publication Data

US 2017/0049020 P1 Feb. 16, 2017

(51) Int. Cl.
*A01H 5/02* (2006.01)

(52) U.S. Cl.
USPC ..... Plt./239

(58) Field of Classification Search
USPC ..... Plt./239
See application file for complete search history.

*Primary Examiner* — Keith Robinson
(74) *Attorney, Agent, or Firm* — The Webb Law Firm

(57) ABSTRACT

A new and distinct *Rhododendron* hybrid plant that exhibits a compact habit and numerous flowers.

4 Drawing Sheets

Botanical classification: *Rhododendron* hybrid.
Varietal denomination: 'Microhirs3'.

BACKGROUND OF THE INVENTION

The present invention comprises a new and distinct cultivar of *Rhododendron* hybrid known by the varietal name 'Microhirs3'. The new variety was discovered in 1997 in Ahrensburg, Germany. The new variety is the result of a planned breeding program, with the intended purpose of providing lime tolerant rootstock varieties, between an unnamed and unpatented *Rhododendron hirsutum* variety (female parent) and an unnamed and unpatented *Rhododendron micranthum* variety (unpatented male parent). 'Microhirs3' exhibits similar corolla form and size to its female parent, but differs from its female parent in flower color and amount. Additionally, 'Microhirs3' exhibits a similar number of flowers per inflorescence to its male parent, but differs from its male parent in corolla color and form. When compared to *Rhododendron* variety 'Intermedium' (unpatented), the new variety is similar in corolla and leaf form, but differs in the color of and amount of flowers. 'Microhirs3' has been trial and field tested and has been found to retain its distinctive characteristics and remain true to type through successive propagations.

DESCRIPTION OF THE DRAWINGS

The accompanying photographic drawings illustrate the new variety at approximately 4 years of age, with the color being as nearly true as is possible with color illustrations of this type.

DESCRIPTION OF THE PLANT

Figure 1:
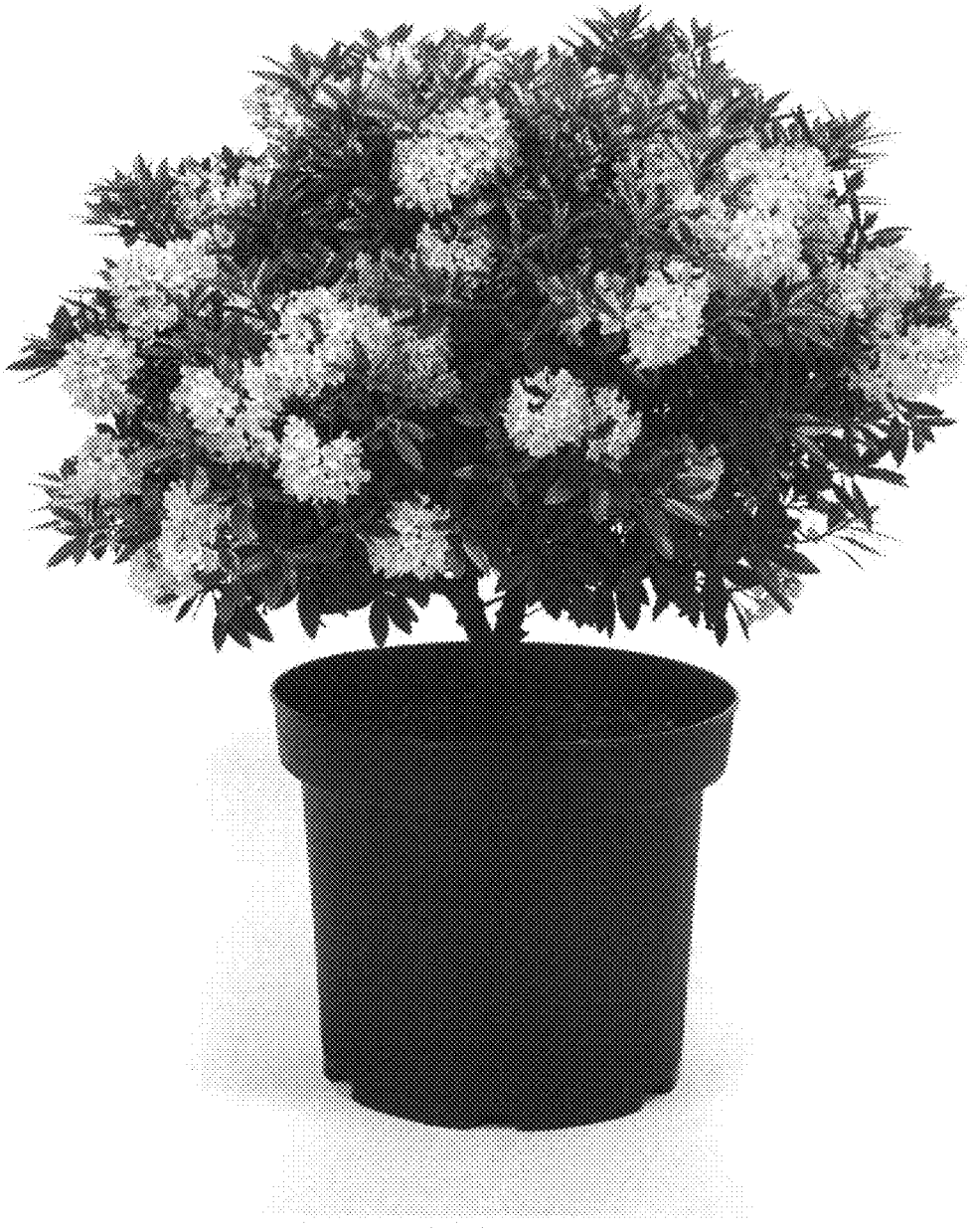
FIG. 1 shows a view of the new variety grown to a flowering plant.
Figure 2:
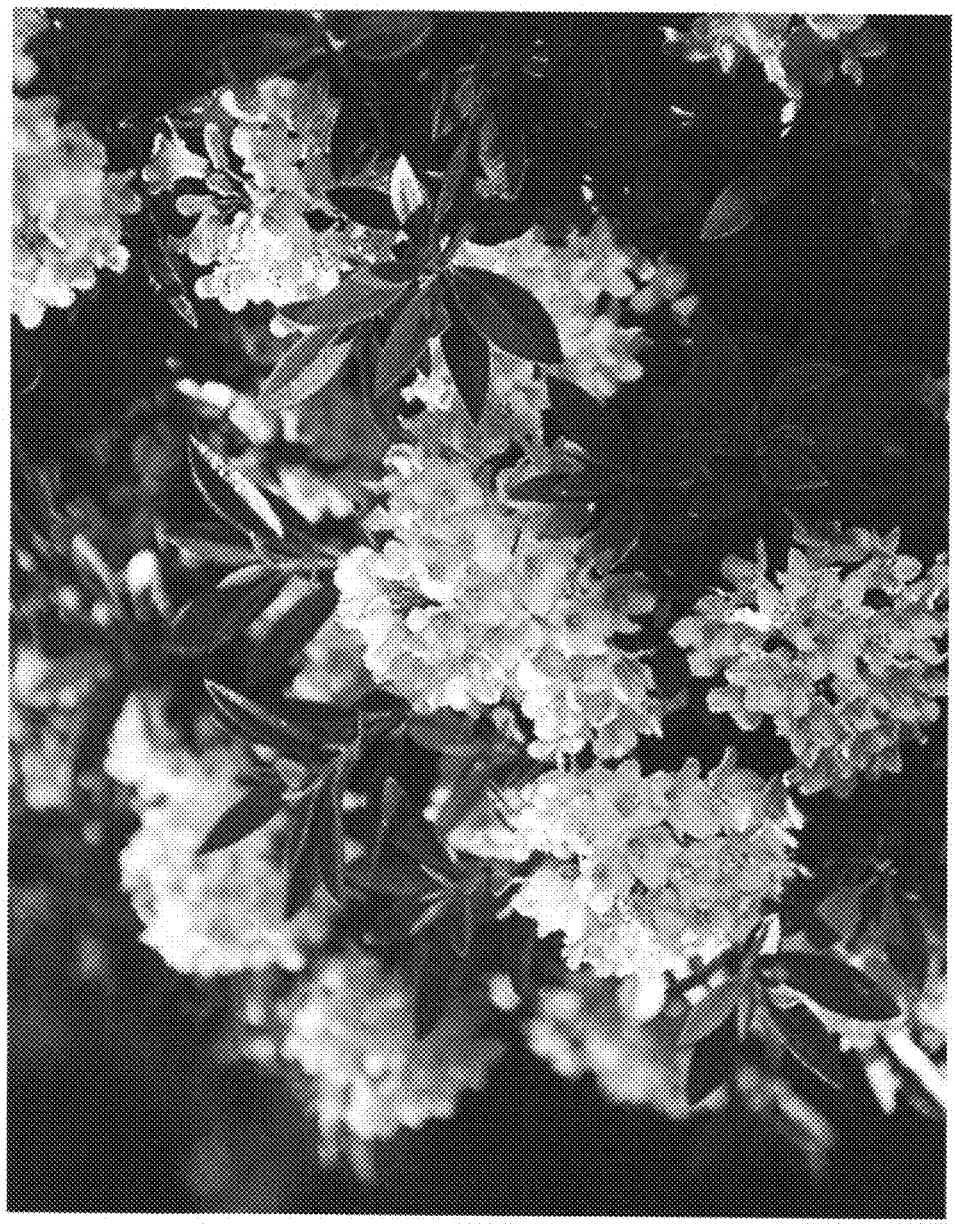
FIG. 2 shows a close-up view of the blooms of the new variety.
Figure 3:
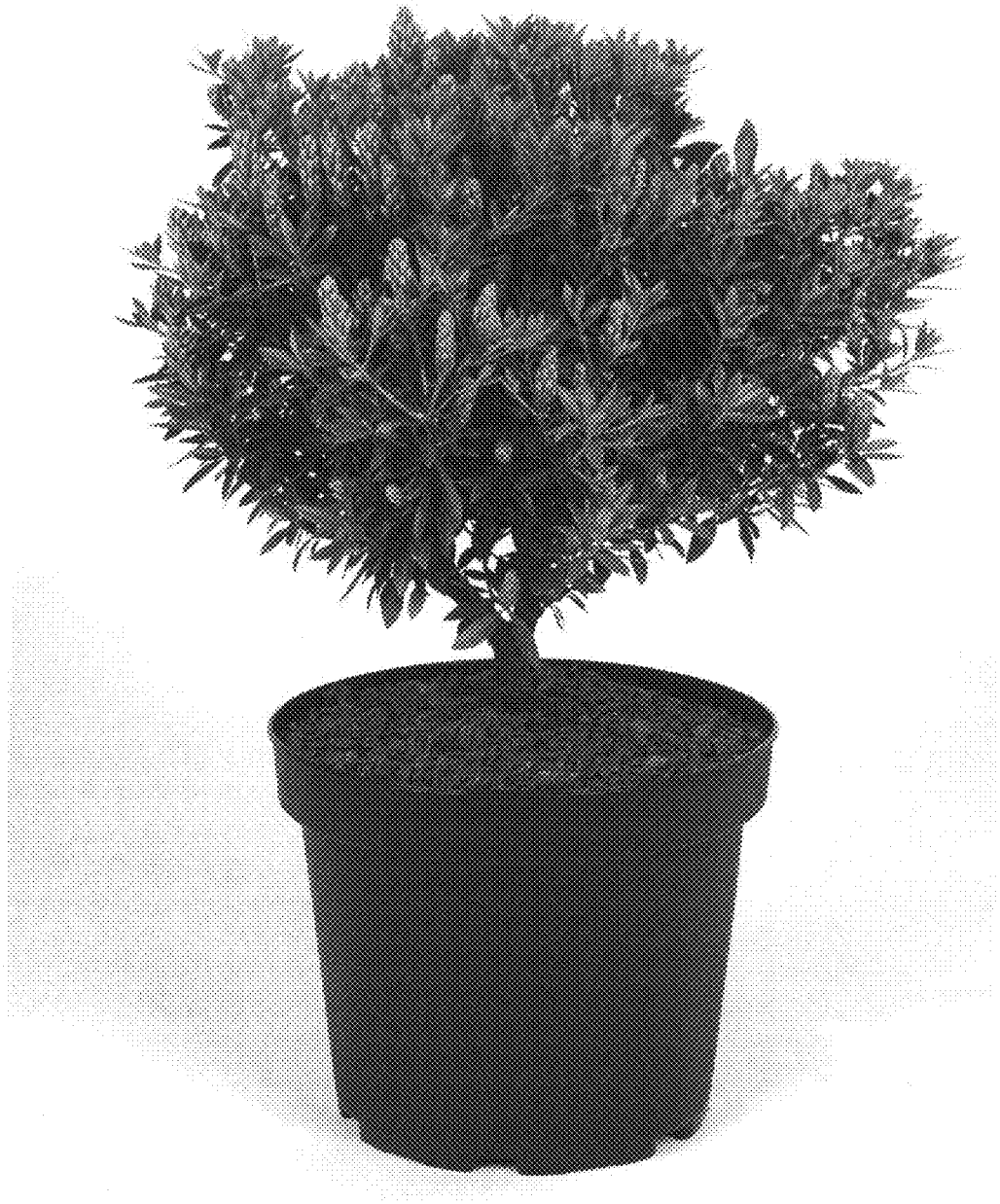
FIG. 3 shows a view of the new variety with unopened buds.
Figure 4:
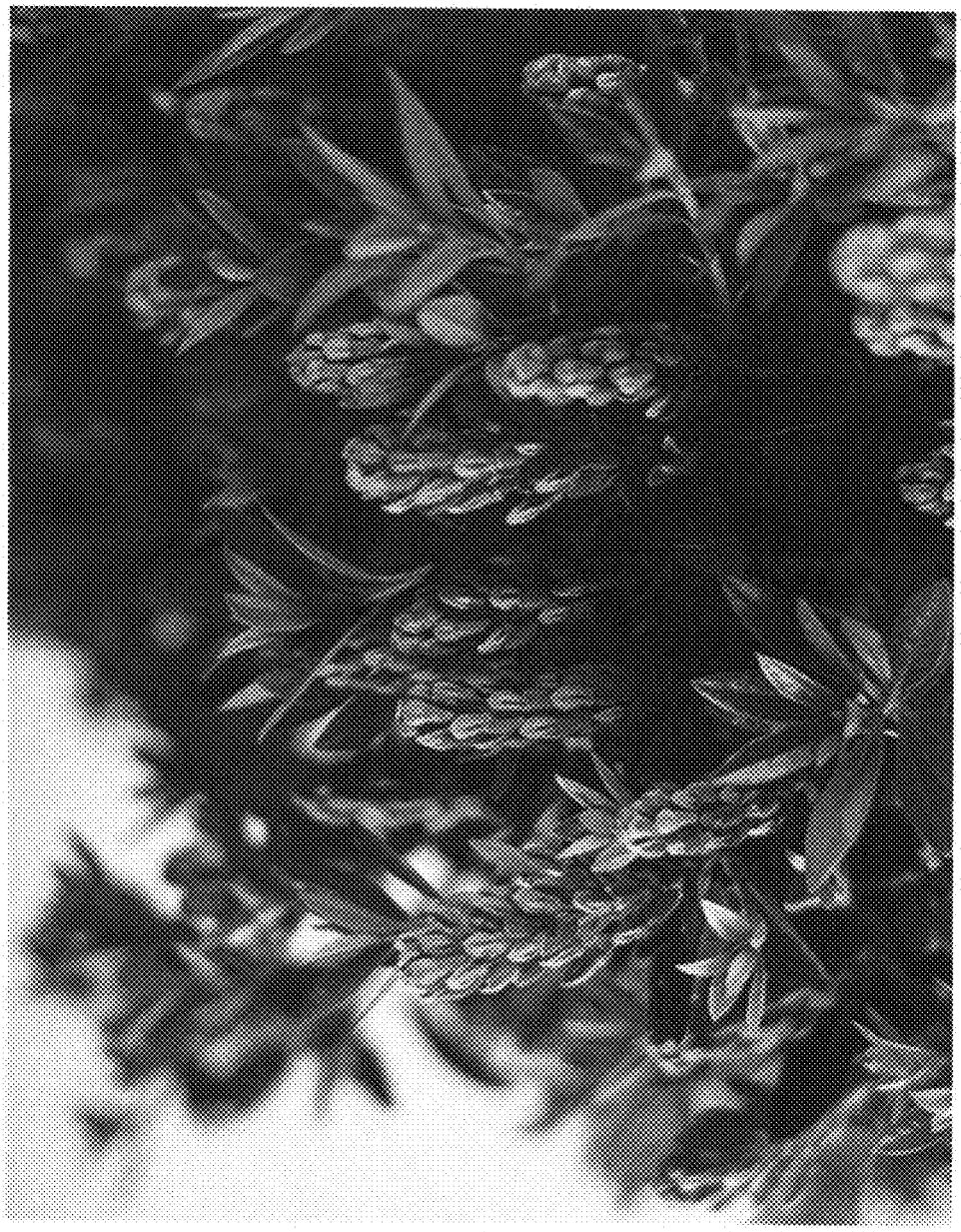
FIG. 4 shows a close-up view of the unopened buds of the new variety.

The following detailed description sets forth the characteristics of the new cultivar. The data which defines these characteristics were collected by asexual reproductions performed via cuttings or in vitro culture in 2003 carried out in Barmstedt, Germany. Plants of the new variety were grown under natural daylight, under typical garden conditions, with yearly mineral and horn shaving applications. The color readings and measurements were taken indoors with a white background behind the variety under a mixture of natural daylight and overhead lighting on 12 year old plants grown in containers. Color references are primarily to The 1986 R.H.S. Colour Chart of The Royal Horticultural Society of London.

PLANT

Time to develop roots: About 50 days at 22-25° C.
Time to produce a finished flowering plant from a rooted cutting: About 110 weeks in a 3 liter container. Thus, flower buds may not appear until 2-3 years after propagation by cutting.
Overall growth habit: Slow, broadly upright, dense, and well-branched.
Rooting habit: Spreading.
Height: 70 cm.
Diameter: 105 cm.
Vigor: Strong, but slow-growing.
Branching habit: Compact and dense.
Disease, temperature, and drought resistance: No observations made to date.
Trunk:
*Diameter:* 0.8-1.3 cm at 30 cm above soil height at 12 years.

*Bark color.*—200C to 200D.
*Texture.*—Hard.
*Pubescence.*—Absent.
*Form.*—Straight, but angular.

Lateral branches:
*Diameter.*—1.5 mm at 1 year; 2 mm at 2 years; 3 mm at 3 years.
*Internode length.*—2-6 mm.
*Texture.*—Flexible in green (144A and 153A) regions, but hard in brown (165B) regions.
*Pubescence.*—None, but scaly.
*Color.*—144A at 1 year; 165B basal and 153A terminal at 2 years.

Leaves:
*Nature.*—Evergreen.
*Arrangement.*—Alternate.
*Length.*—35 mm maximum.
*Width.*—12 mm maximum.
*Shape.*—Lanceolate to broadly lanceolate.
*Apex.*—Acute.
*Base.*—Tapering.
*Margin.*—Entire.
*Texture.*—Generally, smooth and flexible for both leaf surfaces. Mature leaves have an upper surface that is shiny and only slightly scaly and a lower surface that is densely scaly.
*Appearance.*—Glossy and healthy.
*Pubescence* (*both surfaces*).—None, but scaly.
*Color.*—Upper surface: 144A for young leaves and 137A for mature leaves. Lower surface: 137C for young leaves and 146A for mature leaves.
*Venation pattern.*—Net-veined.
*Vein color.*—Upper surface: N144C. Lower surface: N144C.
*Stipules.*—None present.
*Bracts.*—None present.
*Pedicels.*—General description: Round. Length: 21 mm maximum. Width: Approximately 1 mm. Color: 145A.
*Petioles.*—General description: Straight; scaly on lower surface. Length: 5 mm maximum. Diameter: Approximately 1 mm. Color: 144A.

Flowers:
*Natural flowering season.*—End of May until the middle to end of June in Northern Germany.
*Form.*—Short raceme.
*Type.*—Single.
*Overall shape.*—Tubular-campanulate.
*Overall corolla width.*—9-15 mm.
*Overall corolla length.*—12-13 mm.
*Lastingness of bloom.*—Up to three weeks.
*Average number of blooms on a plant.*—Approximately 1,000 on a plant at 12 years.
*Fragrance.*—None.
*Buds* (*described before bursting*).—Shape: Round and tapered. Diameter: 5-7 mm. Length: 5-10 mm. Color: Various — 165B, 167A, and 166C.
*Spike.*—Number of flowers per spike: 20-30. Length: Approximately 3.5-4.5 cm. Diameter: Approximately 4-5 cm.
*Corolla petals.*—Form: Actinomorphic and fused. Shape: Tubular-campanulate. Number: 5. Length: 12 mm maximum. Width: Up to 6 mm. Diameter: Up to 10 mm. Margin: Even to slightly wavy. Texture and appearance: Soft and delicate (both surfaces). Color: When opening: Upper surface: 55B and 55C with 56A, and 155D areas. Lower surface: 62A, with 58C and 58D areas. Fully opened: Upper surface: 155D, with 56B areas. Lower surface: 155D, with 56B and 56C areas.
*Corolla throat.*—Tube length: Approximately 4-5 mm. Color: 155D. Texture: Soft.
*Sepals.*—Form: Single and tapered. Length: 1-2 mm maximum. Shape: Triangular. Apex: Acute. Texture: Hairy, with scales on lower surface.

Reproductive organs:
*Stamens.*—Number: 10. Length: Longer than the pistils. Filament length: 4-9 mm.
*Anthers.*—Shape: Normal *Rhododendron* type. Length: Approximately 1 mm.
*Pollen amount.*—Scarce.
*Pistils.*—Number: 1. Length: Up to 6 mm. Styles: Length: Up to 5.6 mm. Stigmas: Shape: Small and flat.

I claim:

1. A new and distinct variety of *Rhododendron* hybrid plant, as is herein illustrated and described.

* * * * *